United States Patent
Mueller et al.

(10) Patent No.: US 6,172,018 B1
(45) Date of Patent: Jan. 9, 2001

(54) MILD CLEANING PREPARATIONS

(75) Inventors: Reinhard Mueller, Erkelenz; Kurt Seidel, Duesseldorf; Detlef Hollenberg, Erkrath; Anja Patten, Monheim, all of (DE)

(73) Assignee: Henkel Kommanditgesellschaft Auf Aktien, Duesseldorf (DE)

( * ) Notice: Under 35 U.S.C. 154(b), the term of this patent shall be extended for 0 days.

(21) Appl. No.: 08/204,150

(22) PCT Filed: Aug. 24, 1992

(86) PCT No.: PCT/EP92/01940

§ 371 Date: Mar. 2, 1994

§ 102(e) Date: Mar. 2, 1994

(87) PCT Pub. No.: WO93/04662

PCT Pub. Date: Mar. 18, 1993

(30) Foreign Application Priority Data

Sep. 2, 1991 (DE) ................................................ 41 29 124

(51) Int. Cl.[7] ............................... A61K 7/50; A61K 7/40; A61K 7/075; C11D 3/37
(52) U.S. Cl. .................... 510/125; 510/130; 510/137; 510/138; 510/119; 510/127; 510/128; 510/159; 510/470; 510/472; 510/475; 510/476; 510/498
(58) Field of Search ...................... 252/174.17, 174.18, 252/549, 550, 554, 558, 173, DIG. 14

(56) References Cited

U.S. PATENT DOCUMENTS 4,913,828 * 4/1990 Caswell et al. ................. 252/DIG. 5

* cited by examiner

*Primary Examiner*—Mark L. Bell
*Assistant Examiner*—Patricia L. Hailey
(74) *Attorney, Agent, or Firm*—Henry E. Millson, Jr.; John E. Drach; Glenn E.J. Murphy

(57) ABSTRACT

Aqueous cleaning compositions having high foaming power and minimal effect on the skin which comprise (A) from about 1 to about 50% by weight of one or more anionic surfactants having 1 or 2 lipophilic groups each of which has from 1 to 22 carbon atoms and a polar group selected from the group consisting of a carboxylate, a sulfate, and a sulfonate group; (B) from about 0.5 to about 10% by weight of one or more alkyl glycosides of the formula $$R(G)_x$$

wherein R is a linear, saturate $C_{8-22}$ alkyl group, (G) is a glycoside or oligoglycoside moiety, and x is a number from 1 to 4; (C) from about 0.1 to about 5% by weight of an anionic polymer; (D) from about 35 to about 98.4% by weight of water; wherein the sum total of components (B) and (C) is no greater man the amount of component (A).

6 Claims, No Drawings

MILD CLEANING PREPARATIONS

BACKGROUND OF THE INVENTION

1. Field of the Invention

This invention relates to mild cleaning preparations, more particularly for the washing or rinsing of hair.

2. Statement of Related Art

To obtain a cleaning effect, water-containing cleaning preparations normally contain surface-active compounds which generally increase the effect of the preparation on the skin. This applies in particular to the important class of anionic surfactants.

This increased effect on the skin should be avoided in the case of personal hygiene preparations. High skin compatibility is particularly important in the case of products which are designed for frequent use, which are used for washing intimate parts of the body or which come into contact with mucosa. Accordingly, there is a constant need for mild water-containing cleaning preparations with high foaming power.

Preparations for washing or rinsing hair, for example shampoos and hair treatment preparations removable by rinsing, are of particular interest in the field of water-based cleaning preparations. In particular, there is a constant need for preparations which have an improved effect in regard to the fullness and stylability of hair.

The hair is often in a cosmetically unsatisfactory state after washing. It feels dull, is difficult to comb when wet and tends to develop static charges when dry which makes it difficult to comb and affects the set of the hair after combing.

It is known that zwitterionic polymers containing anionic groups, generally carboxyl groups, and quaternary ammonium groups in the molecule can be used in hair treatment preparations. For example, DE-OS-21 50 557 describes the use of polymers of zwitterionic monomers in hair setting preparations. However, zwitterionic polymers are attended by the disadvantage, particularly in formulations containing anionic surfactants, that the hair-conditioning and hair-setting properties are gradually lost in the event of prolonged storage.

DE-OS-33 26 230 describes water-containing preparations for the washing and rinsing of hair which are said to improve the fullness and stylability of the hair through the presence of special polyaldehydocarboxylic acids.

It is also known that conditioning preparations, generally based on cationic surfactants, can be applied to the hair after washing or shampooing and that conditioners can be added to shampoos in order to obtain a certain conditioning effect when the hair is washed. Substances such as these include, for example, cationic polymers, for example cationic cellulose derivatives. European patent application EP 337 354 describes preparations containing a combination of alkyl glycosides and a cationic polymer.

Although it is possible with auxiliaries such as these to obtain a satisfactory improvement in wet combability and, for example with cationic surfactants, a reduction in static charging, these effects are almost always accompanied by excessive smoothing of the dry hair. This gives rise to the disadvantage that the hair lacks fullness and is unable to hold styles. The smoothness of the hair is more pronounced, the lower the combing resistance of the dry hair.

Accordingly, the problem addressed by the present invention was to provide water-containing cleaning preparations, more particularly for the washing and rinsing of hair, which would combine high foaming power with a minimal effect on the skin and which would significantly reduce the smoothness of dry hair without making the hair tacky and without any adverse effect on its wet combability.

DESCRIPTION OF THE INVENTION

It has now surprisingly been found that the fullness and stylability of hair can be distinctly improved in relation to the prior art if the water-containing cleaning preparation contains from 1 to 50% by weight of an anionic surfactant, from 0.5 to 10% by weight of an alkyl glycoside and from 0.1 to 5% by weight of an anionic polymer.

Accordingly, the present invention relates to water-containing cleaning preparations containing (A) 1 to 50% by weight of one or more anionic surfactants containing 1 or 2 lipophilic groups with 1 to 22 carbon atoms and a polar group selected from carboxylate, sulfate or sulfonate groups and optionally a polyoxyalkylene group having an average degree of alkoxylation of 1 to 15, (B) 0.5 to 10% by weight of one or more alkyl glycosides corresponding to the general formula $R(G)_x$ in which R is a linear, saturated $C_{8-22}$ alkyl radical and $(G)_x$ is a glycoside or oligoglycoside having a degree of oligomerization x of 1 to 4, (C) 0.1 to 5% by weight of an anionic polymer, (D) 35 to 98.4% by weight of water, the sum total of components (B) and (C) being no greater than the content of component (A).

In the context of the invention, a polyoxyalkylene group is understood to be a group which is made up of oxyethylene units $-[CH_2-CH-O]-$ or of oxypropylene units $-[CH(CH_3)-CH_2-O]-$. The average number of oxyethylene units or oxypropylene units is termed the average degree of alkoxylation.

According to the invention, the anionic surfactants (A) are preferably selected from the group consisting of alkyl and dialkyl ether sulfates, ether carboxylic acids, sulfosuccinic acid semiesters, fatty alcohol ether citrates, fatty alcohol ether tartrates, acyl sarcosides, acyl taurides and sulfonates of unsaturated fatty acids.

The counterions of the carboxylate, sulfate or sulfonate groups are preferably selected from the group consisting of alkali and alkaline earth metals, aluminium, ammonium and alkyl or alkylolammonium groups containing 1 to 4 carbon atoms in each alkyl or alkylol group. The group of alkali metals is most particularly suitable.

The chemical structures and the basic surfactant properties of most of these anionic surfactants are now established textbook knowledge and, accordingly, require no further explanation. Dialkyl ether sulfates are compounds of the type described in European patent application EP 299 370. Particulars of the production and properties of these compounds can be found in that document. Fatty alcohol ether tartrates are monoester salts of tartaric acid while fatty alcohol ether citrates are monoester and/or diester salts of citric acid with adducts of ethylene oxide and/or propylene oxide with fatty alcohols. Sulfonates of unsaturated fatty acids are sulfonation products of fatty acids containing 12 to 22 carbon atoms and 1 to 6 double bonds. Products such as these are known from the literature and are obtainable, for example, by reaction of these fatty acids with gaseous sulfur trioxide. Taking oleic acid as an example, particulars of their production can be found in German patent application DE 39 26 344.

In the case of anionic surfactants containing a polyoxyalkylene group, it may be stated quite generally with regard to the degree of alkoxylation that alkoxylation reactions such as, for example, the addition of x moles of ethylene oxide onto 1 mole of fatty alcohol by known methods of ethoxylation do not give an adduct per se, but rather a mixture of residues of free fatty alcohol and a series of homologous (oligomeric) addition products of 1, 2, 3, . . . x, x+1, x+2 . . . etc. molecules of ethylene oxide per molecule of fatty alcohol. The average degree of ethoxylation (x) is defined by the starting quantities of fatty alcohol and ethylene oxide. The distribution curve of the homolog mixture generally shows a maximum in the range from x−3 to x+3. Further information on this subject can be found, for example, in the journal *Soap/Cosmetics/Chemical Specialities,* January 1988, page 34. However, in addition to the standard alkoxylation catalysts known from the prior art, such as sodium methanolate, catalysts leading to so-called narrow-range products may also be used (cf. for example *Seifen-Öle-Fette-Wachse* 1990 (116) 60).

In one preferred embodiment of the invention, the percentage content of anionic surfactants is 5 to 30% by weight.

Alkyl glycosides (B) corresponding to the general formula $R-(G)_x$ are well-known surface-active substances which can be produced from sugars and aliphatic primary $C_{8-22}$ alcohols by acetalization. The preferred sugar component (glycose) is glucose, although fructose, mannose, galactose, telose, gulose, allose, altrose, idose, arabinose, xylose, lyxose, libose and mixtures thereof may also be used.

The acetalization products of glucose with fatty alcohols R—OH obtainable by known methods, for example from natural fats and oils, more particularly with linear, primary, saturated and unsaturated $C_{8-22}$ fatty alcohols, are preferred by virtue of their ready availability and their favorable performance properties.

Alkyl glycosides, their production and their use as surfactants are known, for example, from U.S. Pat. No. 3,839,318, U.S. Pat. No. 3,707,535, U.S. Pat. No. 3,547,828, DE-A-1943689, DE-A-2036472, DE-A-3001064 and EP-A-77167. The glycoside $-(G)_x$ may be selected both from monoglycosides (x=1), in which a sugar unit is attached to the fatty alcohol by a glycoside bond, and from oligomeric glycosides having a degree of oligomerization x of 2 to 4. Mixtures of monoglycosides and oligoglycosides are generally present.

Alkyl glycosides (B), in which R is a $C_{8-22}$ alkyl group and $(G)_x$ is a glycoside or oligoglycoside having a degree of oligomerization x of 1 to 4, are particularly suitable. In a particularly preferred embodiment, R is a $C_{10-16}$ alkyl group and $(G)_x$ is the residue of a mixture of glucoside and oligoglucosides having an average degree of oligomerization of 1 to 1.5.

In one preferred embodiment of the invention, the percentage content of the alkyl glycoside is 1 to 5% by weight.

Basically, there are no particular restrictions on the choice of the anionic polymers (C). However, polyaldehydocarboxylic acids having an average molecular weight of 600 to 10,000 and a content of 5 to 9 and preferably 7 to 9 carboxyl groups and 1 to 5 and preferably 1 to 3 aldehyde groups per 10 monomer units have proved to be particularly suitable. These products are used in the form of their water-soluble salts, more particularly their alkali metal salts. Polyaldehydocarboxylic acids such as these are known commercial products. They are prepared, for example, by the oxidative homopolymerization of acrolein or even by the oxidative copolymerization of acrolein and acrylic acid and are marketed, for example, by Degussa AG.

In one preferred embodiment of the invention, the percentage content of the anionic polymer is 0.5 to 3% by weight.

In addition, the preparations according to the invention may contain 0.5 to 20% by weight and, more particularly, 1 to 10% by weight of ampholytic and/or zwitterionic surfactants in addition to the anionic surfactants (A).

Ampholytic surfactants are surface-active compounds which, in addition to a $C_{8-18}$ alkyl or acyl group, contain at least one free amino group and at least one —COOH or —$SO_3$H group in the molecule and are capable of forming inner salts. Examples of suitable ampholytic surfactants are N-alkyl glycines, N-alkyl propionic acids, N-alkyl-aminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids all containing approximately 8 to 18 carbon atoms in the alkyl group.

Zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethyl-ammonium glycinates, for example coconut oil alkyl dimethylammonium glycinate, N-acylaminopropyl-N,N-dimethylammonium glycinate, for example coconut oil acylaminopropyl dimethylammonium glycinate, and 2-alkyl-3-carboxymethyl-3-hydroxyethyl imidazolines containing 8 to 18 carbon atoms in the alkyl or acyl group and also coconut oil acylaminoethyl hydroxyethyl carboxymethyl glycinate.

The gentleness of the preparations according to the invention on the skin is particularly pronounced when the preparations are formulated in such a way that they have a pH value in the vicinity of the neutral point of the skin. Accordingly, preparations having pH values in the range from 4.0 to 7.5 and, more particularly, in the range from 4.5 to 7.0 are preferred.

In addition, the preparations according to the invention may contain inorganic electrolyte salts (E). Suitable inorganic electrolyte salts are any water-soluble alkali metal, ammonium and alkaline earth metal salts, for example the fluorides, chlorides, bromides, sulfates, phosphates and nitrates and hydrogen carbonates, providing they are soluble in water in a quantity of at least 1% by weight at 20° C. The chlorides or sulfates of an alkali metal, ammonium or magnesium are preferably used, sodium chloride and magnesium chloride being particularly preferred. The electrolyte salt is preferably present in a quantity of 0.1 to 10% by weight.

The preparations according to the invention may be used in a number of commercial cleaning products, such as hair shampoos, foam baths, shower baths, liquid soaps and manual dishwashing detergents. They are particularly suitable for mild hair shampoos which leave the hair with improved fullness and stylability.

In addition to surfactants or surfactant combinations, the products in question typically contain such constituents as emulsifiers, oil components, solubilizers, thickeners, superfatting agents, biogenic agents, film formers, fragrances, dyes, pearlescers, foam stabilizers, preservatives and pH regulators. Accordingly, the preparations according to the invention may contain additional components and auxiliaries as known from the prior art. The most important are:

Surfactants/emulsifiers, for example anionic surfactants containing carboxylate, sulfonate, sulfate or phosphate groups, such as soaps, alkyl and aryl ether sulfates, fatty amines, quaternary ammonium and pyridinium compounds, nonionic emulsifiers, such as ethylene oxide adducts with alcohols, carboxylic acids, partial glycerides and sorbitan esters, amphoteric and zwitterionic emulsifiers, such as imidazoline derivatives, betaines or sulfobetaines and, for example, fatty acid esters and sorbitan fatty acid esters (cf. for example W. Umbach [Ed.] *"Kosmetik-Entwicklung, Herstellung und Anwendung kosmetischer Mittel"*, pages 86–87, Stuttgart 1988).

Oil components, for example substances such as paraffin oil, vegetable oils, fatty acid esters, squalane and 2-octyl dodecanol; as fats and waxes, for example spermaceti, beeswax, montan wax, paraffin and cetostearyl alcohol.

Solubilizers, for example lower monohydric or polyhydric alcohols, such as ethanol, isopropanol, ethylene glycol, propylene glycol, glycerol, 1,3-butylene glycol and diethylene glycol.

Thickeners, for example polysaccharides, more particularly xanthan gum, guar gum, agar agar, alginates and tyloses; carboxymethyl cellulose and hydroxyethyl cellulose; relatively high molecular weight polyethylene glycol monoesters and diesters of fatty acids, polyacrylates, polyvinyl alcohol and polyvinyl pyrrolidone.

Superfatting agents, for example polyethoxylated lanolin derivatives, lecithin derivatives and fatty acid alkanolamides, the latter also acting as foam stabilizers.

Biogenic agents, such as plant extracts, protein degradation products and vitamin complexes.

Film formers, such as polyvinyl pyrrolidone, vinyl pyrrolidone/vinyl acetate copolymers, polymers of the acrylic acid series, quaternary cellulose derivatives and similar compounds.

Humectants, for example glycerol, polyglycerols, sorbitol, propane-1,2-diol, butane-1,2,3-triol, polyethylene glycols, glucose, mannitol, xylitol, pyrrolidone carboxylic salts (PCA), amino acids, lactic acid.

Antimicrobial agents as preservatives, for example benzoic acid, salicylic acid, sorbic acid, esters and salts thereof and the substances listed in the *"Anlage zur Kosmetikverordnung (Appendix to the Cosmetics Act)"*.

Pearlescers, such as glycol distearic acid esters, ethylene glycol distearate or fatty acid monoglycol esters.

Fragrances, for example natural fragrances obtained from plants by distillation, extraction or pressing and synthetic fragrances (cf. for example H. Aebi, E. Baumgartner, H. P. Fiedler, G. Ohloff, *"Kosmetika, Riechstoffe und Lebensmittelzusatzstoffe"*, Stuttgart 1978).

Antioxidants, for example tocopherols, lecithin, guaiacol, butyl cresol, 4-methyl-2,6-ditert.butylphenol (BHT), 4-methoxy-2(3)tert.butylphenol (BHA).

Dyes as listed, for example, by the Farbstoff-Kommission der Deutschen Forschungsgemeinschaft für Kosmetika (*"Färbemittel für Kosmetika"* Mitteilung 3, Wiesbaden 1968). The dyes are typically used in concentrations of 0.001 to 0.1% by weight, based on the mixture as a whole.

pH regulators: other components of the preparations according to the invention are, if desired, substances of which the function is to adjust the pH value of the preparations.

The auxiliaries are present in total quantities of 0 to 20% by weight and preferably 0 to 10% by weight.

To produce the preparations according to the invention, the alkyl glycoside (B) is added at 60 to 80° C. to an aqueous phase containing the anionic surfactants (A), the anionic polymer (C) and the electrolyte salt (D). These mixtures are stirred and then cooled to normal temperature (20 to 40° C.). By virtue of the water solubility of the alkyl glycosides, particularly those containing $C_{12-16}$ alkyl groups, the preparations according to the invention may also be produced with advantage in the absence of heat. In this case, the components are merely stirred together at normal temperature.

The following Examples are intended to illustrate the invention without limiting it in any way.

EXAMPLES

1. General 1.1. Abbreviations

In the headings of Tables 1 to 5, the Examples according to the invention are identified as E1 to E5 while the Comparison Examples are identified as C1 to C10.

1.2. Substances used 1.2.1. Surfactants

N25: Aqueous solution of sodium lauryl ether sulfate; active substance content: 28% by weight ("Texapon® N25"; a product of Henkel KGaA, Düsseldorf) 1, Dehyton K: Aqueous solution of a fatty acid amide derivative of betaine structure with the formula R—CONH—$(CH_2)_3$—$N^+(CH_3)_2$—$CH_2$—$COO^-$; CTFA name: Cocamidopropyl Betaine; active substance content: 30% by weight; NaCl content: 5% by weight (a product of Henkel KGaA, Düsseldorf)

AKYP: Aqueous solution of an ether carboxylic acid salt with the formula $C_{12/14}$—$(O-CH_2-CH_2)_{10}$—$OCH_2$—COONa, active substance content: 22% by weight ("Akypo®-Soft 100 NV"; a product of Chemy-Y)

APG600: $C_{12/14}$ fatty alcohol glucoside with a degree of oligomerization of 1.45 (a product of Henkel KGaA, Düsseldorf).

1.2.2. Other substances

Nutrilan I: Protein hydrolyzate; CTFA name: Hydrolyzed Animal Collagen ("Nutrilan® I"; a product of Grünau, Illertissen)

POC: Aqueous solution of poly(aldehydocarboxylic acid) sodium salt; active substance content: 40% by weight; average molecular weight: 5,000 ("POC-HS-5060"; a product of Degussa AG)

2. Determination of dry combability

The combability tests were based on the method described in J. Soc. Cosm. Chem. 1973 [24] 782.

Dry combability was tested on brown hair (Alkinco #6634, tress length 12 cm, tress weight 1 g). The hair used was slightly predamaged (bleached) hair as might be expected of the average user. After the zero measurement, the tresses were soaked with 100 ml of the formulation to be tested. After a contact time of 5 minutes, the tresses were rinsed for 1 minute in running water (1 l/min., 38° C.). The tresses were then dried for 12 hours at 30° C./20% relative air humidity and thereafter were remeasured and the results were compared with the zero measurement. The results of the dry combability tests are set out in Table 1.

TABLE 1

| | Dry combability[(1)] | | |
|---|---|---|---|
| Substance | C1 | C2 | E1 |
| N25 | 9.0 | 9.0 | 9.0 |
| AKYP | 3.0 | 3.0 | 3.0 |
| Dehyton K | 3.0 | 3.0 | 3.0 |
| Nutrilan I | 0.5 | 0.5 | 0.5 |
| POC | — | 1.0 | 1.0 |
| APG 600 | — | — | 2.0 |
| Water | ad 100 | ad 100 | ad 100 |
| DC (%)[(2)] | 95 | 122 | 146 |

TABLE 1-continued

| | Dry combability[1] | | |
|---|---|---|---|
| Substance | C1 | C2 | E1 |

[1]The figures in the upper block of the Table represent % by weight of active substance. The figures in the lower block of the Table represent the experimentally determined dry combability DC value by comparison with the zero measurement.
[2]The statistical certainty of the DC values was 99.99%.

Example E1 according to the invention shows distinctly higher dry combability than C1 and C2. Since DC is a measure of style holdability, E1 shows an improvement in style holdability.

3. Determination of wet combability

The combability tests were based on the method described in J. Soc. Cosm. Chem. 1973 [24] 782.

Wet combability was tested on brown hair (Alkinco #6634, tress length 12 cm, tress weight 1 g). The hair used was slightly predamaged (bleached) hair as might be expected of the average user. After the zero measurement, the tresses were soaked with 100 ml of the formulation to be tested. After a contact time of 5 minutes, the tresses were rinsed for 1 minute in running water (1 l/min., 38° C.). The tresses were then remeasured and the results were compared with the zero measurement. The results of the wet combability tests are set out in Table 2.

TABLE 2

| | Wet Combability[1] | | |
|---|---|---|---|
| Substance | C3 | C4 | E2 |
| N25 | 9.0 | 9.0 | 9.0 |
| AKYP | 3.0 | 3.0 | 3.0 |
| Dehyton K | 3.0 | 3.0 | 3.0 |
| Nutrilan I | 0.5 | 0.5 | 0.5 |
| POC | — | 1.0 | 1.0 |
| APG 600 | — | — | 2.0 |
| Water | ad 100 | ad 100 | ad 100 |
| WC (%)[2] | 94 | 92 | 80 |

[1]The figures in the upper block of the Table represent % by weight of active substance. The figures in the lower block of the Table represent the experimentally determined wet combability WC value by comparison with the zero measurement.
[2]The statistical certainty of the WC values was 99.99%.

Example E2 according to the invention shows a distinctly lower wet combability value by comparison with C3 and C4. Since lower WC values signify a better combability of wet hair, E2 shows an improvement in wet combability.

4. Electrostatic charging

To determine electrostatic charging during combing, a hair tress was suspended in a double Faraday cage. There was no conductive connection between the inner and outer cages. The outer cage was connected to a zero potential (ground). A voltmeter measured potential differences between the inner and outer cages. Potential differences always arise when, under the effect of friction during combing, charges are displaced from the surfaces of the hair fibers and collect on the surface of the comb. The electrical field and the tresses oppositely charged by comparison with the comb interact with the inner Faraday cage. The inner Faraday cage develops an opposite charge on the inside (influence). The charge displacement relative to the outer cage was recorded on the voltmeter and was a direct measure of the triboelectric charging of the combed hair tresses.

TABLE 3

| | Electrostatic charging[1] | | |
|---|---|---|---|
| Substance | C5 | C6 | E3 |
| N25 | 9.0 | 9.0 | 9.0 |
| AKYP | 3.0 | 3.0 | 3.0 |
| Dehyton K | 3.0 | 3.0 | 3.0 |
| Nutrilan I | 0.5 | 0.5 | 0.5 |
| POC | — | 1.0 | 1.0 |
| APG 600 | — | — | 2.0 |
| Water | ad 100 | ad 100 | ad 100 |
| EC (%) | 92 | 90 | 73 |

[1]The figures in the upper block of the Table represent % by weight of active substance. The figures in the lower block of the Table represent the experimentally determined electrostatic charging EC values by comparison with the zero measurement.

Example E3 according to the invention shows a considerably lower electrostatic charging value by comparison with C5 and C6. Lower EC values signify a reduced tendency of the hair fibers to repel and to "fly away" from one another.

5. Determination of foaming behavior

The foaming behavior of the cleaning preparations was determined with a motorized foam generating apparatus in accordance with DIN 53 902. To this end, 340 ml of a solution were prepared by diluting the water-containing cleaning preparation with tapwater from Düsseldorf Holthausen (hardness=18° dH) in such a way that it contained 2% by weight active substance of surfactants. The foam was produced at room temperature using a perforated plate (bores 1 mm in diameter, 10 beats at a frequency of 50 beats per minute, 13 cm stroke). The foam was very fine and thus largely corresponded to the foam formed on the hair during shampooing. The measurements were carried out as double determinations with no fats in the surfactant solution.

The foaming behavior of a known high-foaming mixture of (a) 42% by weight of Texapon N 25
   (=12% of active substance)
(b) 10% by weight of Dehyton K
   (=3% of active substance)
(c) 1% by weight of Comperlan LS
   (=1% of active substance) and
(d) 47% by weight of water was determined as standard. This standard mixture was diluted with water and was also used in the form of a solution containing 2% by weight of active substance. The following quantities of foam were measured:

after 1 minute: 240 ml
after 3 minutes: 210 ml
after 5 minutes: 190 ml

TABLE 4

| | Relative quantity of foam | | |
|---|---|---|---|
| Substance | C7 | C8 | E4 |
| N25 | 9.0 | 9.0 | 9.0 |
| AKYP | 3.0 | 3.0 | 3.0 |
| Dehyton K | 3.0 | 3.0 | 3.0 |
| Nutrilan I | 0.5 | 0.5 | 0.5 |
| POC | — | 1.0 | 1.0 |
| APG 600 | — | — | 2.0 |
| Water | ad 100 | ad 100 | ad 100 |
| Foam 1' | 87 | 95 | 105 |

TABLE 4-continued

| | Relative quantity of foam | | |
|---|---|---|---|
| Substance | C7 | C8 | E4 |
| Foam 3' | 95 | 89 | 100 |
| Foam 5' | 94 | 88 | 113 |

[1]The figures in the upper block of the Table represent % by weight of active substance of the water-containing cleaning preparation before further dilution with water to form a solution containing 2% active substance of surfactants. The figures in the lower block of the Table represent the percentage quantity of foam compared with the standard.

Example E4 according to the invention shows a distinctly larger quantity of foam by comparison with C7 and C8.

6. Skin compatibility tests

The skin compatibility of the cleaning preparations was determined by the in vitro method developed by Zeidler and Reese which is described in detail in the journal Ärztliche Kosmetologie 13, 39–45 (1983). The swelling of porcine epidermis was used as a measure of the skin compatibility of the cleaning preparations. To this end, the epidermis required was taken from freshly slaughtered young pigs and deep frozen.

For the measurement, epidermis strips measuring 1 cm×6 cm were cut out and immersed for 30 minutes in a solution which had been prepared by diluting the water-containing cleaning preparation with water in such a way that it contained 2% by weight active substance of surfactants. The solution was kept at 39° C. and adjusted to pH 6.5. After brief rinsing and removal of the adhering water by gentle pressing under defined conditions, the weight of the swollen strips was determined. The strips were then dried over calcium chloride for 24 hours and reweighed. In order to eliminate influences attributable to specific properties of the particular animal and the point of removal (back, flank), a standard measurement was carried out in each case. To this end, an immediately adjacent epidermis strip is similarly treated with water instead of the water-containing cleaning preparation.

The measured values s for the surfactant treatment and w for the treatment with water are derived from the following relation:

$$s, w = \frac{\text{weight (swollen epidermis)} - \text{weight (dry epidermis)}}{\text{weight (dry epidermis)}}$$

Finally, the standardized relative change in swelling Q is defined as $$Q = (s/w - 1) \cdot 100\%$$

By definition, therefore, the Q value of the water-treated skin is 0%. Negative values indicate swelling-inhibiting properties.

The results of the swelling measurements are set out in Table 5. It was found that Example E5 according to the invention shows improved swelling values by comparison with C9 and C10.

TABLE 5

| | Swelling measurements[1] | | |
|---|---|---|---|
| Substance | C9 | C10 | E5 |
| N25 | 9.0 | 9.0 | 9.0 |
| AKYP | 3.0 | 3.0 | 3.0 |
| Dehyton K | 3.0 | 3.0 | 3.0 |
| Nutrilan I | 0.5 | 0.5 | 0.5 |
| POC | — | 1.0 | 1.0 |
| APG 600 | — | — | 2.0 |
| Water | ad 100 | ad 100 | ad 100 |
| Swelling value[2] | 50 | 44 | 24 |

[1]The figures in the upper block of the Table represent % by weight of active substance of the water-containing cleaning preparation before further dilution with water to form a solution containing 2% active substance of surfactants. The figures in the lower block of the Table represent the experimentally determined swelling value Q.
[2]In all the tests, the margin of error was ± 7.

What is claimed is:

1. An aqueous cleaning composition comprising: (A) from about 1 to about 50% by weight of one or more anionic surfactants having 1 or 2 lipophilic groups each of which has from 1 to 22 carbon atoms and a polar group selected from the group consisting of a carboxylate, a sulfate, and a sulfonate group; (B) from about 0.5 to about 10% by weight of one or more alkyl glycosides of the formula $$R(G)_x$$

wherein R is a linear, saturated $C_{8-22}$ alkyl group, (G) is a glycoside or oligoglycoside moiety, and x is a number from 1 to 4; (C) from about 0.1 to about 5% by weight of an anionic polymer; (D) from about 35 to about 98.4% by weight of water; wherein the sum total of components (B) and (C) is no greater than the amount of component (A).

2. The composition of claim 1 wherein said anionic surfactant is further comprised of a polyoxyalkylene group having an average degree of alkoxylation of 1 to 15.

3. The composition of claim 1 wherein the amount of said anionic surfactant is from about 5 to about 30% by weight.

4. The composition of claim 1, wherein the amount of said alkyl glycoside is from about 1 to about 5% by weight.

5. The composition of claim 1 wherein the amount of said anionic surfactant is from about 0.5 to about 3.0% by weight.

6. The composition of claim 1 further comprising from about 0.1 to about 10% by weight of an anionic electrolyte salt.

* * * * *